United States Patent [19]

Ashina et al.

[11] Patent Number: 4,844,809
[45] Date of Patent: Jul. 4, 1989

[54] METHOD FOR PURIFYING REACTION SOLUTION OBTAINED BY USING MICROBIAL CELL, IMMOBILIZED MICROBIAL CELL, OR IMMOBILIZED ENZYME

[75] Inventors: Yoshiro Ashina; Yasumasa Yamaguchi; Masashi Nishida; Toshiaki Doi, all of Kanagawa, Japan

[73] Assignee: Nitto Chemical Industry Co., Ltd., Tokyo, Japan

[21] Appl. No.: 799,059

[22] Filed: Nov. 18, 1985

[30] Foreign Application Priority Data

Nov. 16, 1984 [JP] Japan ................................ 59-240845

[51] Int. Cl.$^4$ ............................................. B01D 13/00
[52] U.S. Cl. ................................ 210/636; 210/500.23; 210/651
[58] Field of Search ................. 435/70; 210/636, 651, 210/500.23

[56] References Cited

U.S. PATENT DOCUMENTS 4,614,717  9/1986  Kachholz et al. ................ 435/70 X

FOREIGN PATENT DOCUMENTS 0057185  5/1978  Japan .................................. 210/636
0024006  3/1981  Japan .................................. 210/636

*Primary Examiner*—Frank Spear
*Attorney, Agent, or Firm*—Sughrue, Mion, Zinn, Macpeak, and Seas

[57] ABSTRACT

A method for purifying a reaction solution obtained by using a microbial cell, an immobilized microbial cell, or an immobilized enzyme as a catalyst in a water medium is disclosed. The method comprises repeatedly filtering the reaction solution to remove fine solid matter using a polyethylene porous hollow fiber membrane having a bubble point of from 1 to 20 kg/cm$^2$, and repeatedly washing the hollow fiber membrane before it has been clogged to such an extent that a differential pressure thereof exceeds 3 kg/cm$^2$. By this method, a filter membrane can be repeatedly regenerated at high efficiency and can stably be used for a long period of time.

16 Claims, No Drawings

METHOD FOR PURIFYING REACTION SOLUTION OBTAINED BY USING MICROBIAL CELL, IMMOBILIZED MICROBIAL CELL, OR IMMOBILIZED ENZYME

FIELD OF THE INVENTION

This invention relates to a method of purifying a reaction solution (hereinafter, aqueous solution) obtained by using a microbial cell, an immobilized microbial cell (hereinafter, immobilized cell), or an immobilized enzyme as a catalyst in a water medium.

This invention is suitably applicable to purification of an aqueous acrylamide solution that can not be subjected to a pretreatment, such as heat treatment or acid-treatment, because of its tendency to polymerize, or cannot be treated with a coagulant, etc., to remove fine solid matters from the standpoint of product quality, and is particularly applicable to an aqueous acrylamide solution obtained by using an immobilized cell or immobilized enzyme (hereinafter, immobilized cell, etc.).

BACKGROUND OF THE INVENTION

It is known that impurities contained in an aqueous medium including fine solid matter can be removed by filtering the aqueous medium using a porous hollow fiber membrane composed of polyvinyl alcohol, and the hollow fiber membrane clogged with impurities can be regenerated for reuse by washing with an acid and/or alkali as disclosed in Japanese Patent Publication No. 37037/83.

However, the above-described method requires a large quantity of an acid and/or alkali every time the filter is regenerated, and, therefore, involves handling of a large quantity of a highly concentrated acid or alkali waste water. In addition, the extent of restoration of filterability achieved by regeneration with an acid or alkali is not totally satisfactory. Hence, this method is not satisfactory for industrial application.

When a reaction is carried out in an aqueous medium in the presence of a microbial cell, an immobilized cell, etc., as a catalyst, the resulting aqueous solution from which the catalyst has been removed by filtration sometimes has a slight turbidity. Such turbidity should be removed before merchandising of the aqueous solution as such or in the form of a concentrate. This turbidity is attributed to fine solids suspended in the aqueous solution, and it is not easy to remove this solid matter through conventional filtration. Removal of the fine solids filtration can be achieved only with a filter membrane having a pore size as fine as 1 $\mu$m or less, but a membrane having such a small pore size is soon clogged, and thus has a short working life.

For removing fine particles, filterability may be improved by pretreatment of the aqueous solution, such as heat treatment and acid treatment, or addition of a coagulant to the aqueous solution. However, these techniques cannot be applied to substances that are easily polymerized or required to have high quality, such as acrylamide as described before, and removal of turbidity forms a particular subject. Although addition of a coagulant flocculates fine particles in an aqueous solution to improve filterability, a part of the coagulant added remains in the aqueous solution to deteriorate product quality.

Hence, it is keenly demanded based on industrial considerations that a clogged filter membrane be repeatedly regenerated at high efficiency so as to be used for a long period of time.

SUMMARY OF THE INVENTION

Accordingly, the present invention is directed to a method for purifying a reaction solution obtained by using a microbial cell, an immobilized cell, or an immobilized enzyme as a catalyst in a water medium, which comprises repeatedly filtering the reaction solution to remove fine solid matter using a polyethylene porous hollow fiber membrane having a bubble point of from 1 to 20 kg/cm$^2$ (determined in ASTM F316-70) and repeatedly washing the hollow fiber membrane before it has been clogged to such an extent that a differential pressure thereof exceeds 3 kg/cm$^2$.

The porous hollow fiber membrane to be used in the present invention is excellent in chemical resistance as well as durability against back washing pressure or vibration repeatedly applied during washing, and, therefore, withstands repetition of filtration and washing and use for a prolonged period of time.

DETAILED DESCRIPTION OF THE INVENTION

The porous hollow fiber membrane which can be used in the present invention is made of polyethylene hollow fiber having a diameter of from 0.2 to 2 mm, and preferably from 0.3 to 1 mm. A preferred length of the fiber is from 40 to 200 cm from the standpoint of washing efficiency. A bundle comprising at least 100, and usually from 1,000 to 20,000 fibers is fixed to a filter. The membrane thickness provides influences on pressure resistance, trapping performance, and permeability of the membrane, and preferably ranges from 0.02 to 0.2 mm.

Fine pores of the polyethylene hollow fiber membrane have a slit shape. The pore size is expressed in terms of gas flux obtained by determining the amount of filtered air under a given pressure and bubble point (determined in ASTM F316-70) obtained by immersing a hollow fiber membrane in water, applying air pressure to the inside of the fiber and determining the pressure that generates bubbles. In the present invention, the hollow fiber membrane should have a bubble point of from 1 to 20 kg/cm$^2$, and preferably from 2 to 8 kg/cm$^2$, in view of performances required to trap solid matter and to regenerate the clogged membrane. A preferred gas flux of the hollow fiber membrane is from $8 \times 10^4$ to $30 \times 10^4$ l/m$^2$.hr.0.5 atm.

In carrying out the present invention, conditions for filtration of the aqueous solution and the degree of clogging of the membrane to be regenerated are important factors for lightening the labor of washing. The aqueous solution is generally filtered at a rate of from 2 to 1,000 l/m$^2$.hr, and preferably from 10 to 200 l/m$^2$.hr. The preferred degree of clogging of the membrane when subjected to regeneration washing is such as to have a differential pressure of from 0.5 to 3 kg/cm$^2$, and more preferably from 0.7 to 1.2 kg/cm$^2$. If the differential pressure of the hollow fiber membrane exceeds 3 kg/cm$^2$, regeneration becomes difficult.

Washing of the clogged hollow fiber membrane can usually be carried out by so-called back washing, in which water is made to run in the direction opposite to the filteration direction. A greater washing effect may be obtained by passing a large quantity of water, to result in a greater differential pressure, but the differential pressure during the washing is usually set at from 1 to 10 kg/cm$^2$, and preferably from 2 to 4 kg/cm$^2$, from the viewpoint of durability of the hollow fiber membrane.

After repetition of regeneration by back washing several times, recovery of filterability becomes poor. If the hollow fiber membrane is exchanged with fresh one at this point, such entails cost, giving rise to a serious problem. Such a hollow fiber membrane that may not be sufficiently regenerated any longer simply by back washing, can, therefore, be subjected to chemical treatment by immersing in an alkali, an acid, an alcohol, etc., followed by back washing with water to thereby effectively remove the clogging from the membrane. Inter alia, alkali-treatment is preferred. The fact that filterability can be restored particularly by alkali-treatment is an unexpected result seeing that the fine solid matter leaked out from an immobilizing material used for immobilizing microbial cells or enzymes is generally insoluble in an alkali.

The alkali-treatment can be carried out, for example, with an aqueous sodium hydroxide solution at a concentration of from 2 to 30% by weight, and preferably from 5 to 15% by weight. A filter fitted with the hollow fiber membrane having been subjected to back washing is filled with the above-described aqueous sodium hydroxide solution and allowed to stand for from 0.1 to 100 hours, and preferably for from 1 to 40 hours. Thereafter, the membrane is back-washed with water under the same conditions as described before. Higher alkali concentrations make the time for alkali-treatment shorter, but require greater amounts of the alkali. Accordingly, the above-recited conditions are suitable.

In addition, washing of a clogged hollow fiber membrane may appropriately be effected by bubbling with air, etc., or vibration by ultrasonic waves.

The present invention is preferably applied to a reaction solution obtained by using an immobilized cell or an immobilized enzyme.

The present invention will now be illustrated in greater detail with reference to the following examples, but it should be understood that these examples are not limiting the present invention. In these examples, all the parts and percents are by weight unless otherwise indicated.

EXAMPLE 1

A microorganism belonging to the genus Corynebacterium and capable of hydrating a nitrile, N-774 strain (FERM-P No. 4446), was aerobically cultivated in a medium (pH 7.2) containing 1% glucose, 0.5% peptone, 0.3% yeast extract, 0.3% malt extract, and 0.05% ferric sulfate heptahydrate. Forty parts of a washed microbial cell collected from the culture (water content: 75%), 45 parts of acrylamide, 0.5 part of N,N'-methylenebisacrylamide and 40 parts of a 0.05M phosphoric acid buffer (pH 7.7) were mixed to form a uniform suspension. To the suspension were added 5 parts of a 5% aqueous solution of dimethylaminopropionitrile and 10 parts of a 2.5% aqueous solution of potassium persulfate, and the resulting mixture was maintained at 10° C. for 30 minutes to effect polymerization. The resulting massive gel containing the microbial cell was crushed to small particles and thoroughly washed with a 0.05M phosphoric acid buffer (pH 7.7) to obtain 100 parts of an immobilized cell.

Water and acrylonitrile were reacted at 0° C. in the presence of the above prepared immobilized cell in a continuous reactor equipped with a stirrer to obtain a 20% aqueous solution of acrylamide. Separation of the immobilized cell from the reaction solution was carried out by filtration using an 80 mesh metal netting and a 5-μm-yarn reel filter. The resulting aqueous solution was found to contain 0.5 ppm of solid matter.

The resulting 20% aqueous solution of acrylamide was filtered using a polyethylene-made porous hollow fiber membrane (hollow fiber membrane: EHF 390c, a trademark of a product produced by Mitsubishi Rayon Co., Ltd.) having a filtration area of 0.3 m$^2$ and a bubble point of 4.8 kg/cm$^2$ at a rate of 8 l/hr.

When the differential pressure of the hollow fiber membrane reached about 0.9 kg/cm$^2$ due to clogging, the membrane was subjected to back washing with water at a pressure of 4 kg/cm$^2$, and then was reused for filtration. After the membrane was used for filtration and back-washed four times, it was immersed in a 12% aqueous solution of sodium hydroxide for 15 hours, back-washed with water, and then reused for filtration. The differential pressures across the hollow fiber membrane after the repeated filtration and regeneration as described above are shown in Table 1.

The thus obtained aqueous acrylamide solution was found to contain 0.01 ppm of a solid matter.

Table 1

| Number of Filtration | Differential Pressure | |
|---|---|---|
| | Before Washing (kg/cm$^2$) | After Washing (kg/cm$^2$) |
| 0 | 0.25 | — |
| 1 | 0.90 | 0.33 |
| 2 | 0.92 | 0.36 |
| 3 | 0.93 | 0.40 |
| 4 | 0.95 | 0.33* |
| 5 | 0.89 | 0.35 |
| 6 | 0.90 | 0.37 |
| 7 | 0.95 | 0.40 |
| 8 | 0.95 | 0.34* |
| 9 | 0.91 | 0.35 |
| 10 | 0.91 | 0.37 |
| 11 | 0.93 | 0.40 |
| 12 | 0.94 | 0.34* |
| 13 | 0.90 | 0.36 |
| 14 | 0.92 | 0.37 |
| 15 | 0.92 | 0.41 |
| 16 | 0.94 | 0.34* |
| 17 | 0.90 | 0.36 |
| 18 | 0.91 | 0.37 |
| 19 | 0.93 | 0.39 |
| 20 | 0.95 | — |
| 21 | — | — |

Note:
*Alkali-treatment was performed in combination with back washing with water

COMPARATIVE EXAMPLE 1

The same procedures as described in Example 1 were repeated, except that the back washing of the clogged hollow fiber membrane was conduted every time the differential pressure of the membrane reached about 4 kg/cm$^2$. The results obtained are shown in Table 2 below.

TABLE 2

| Number of Filtration | Differential Pressure | |
|---|---|---|
| | Before Washing (kg/cm$^2$) | After Washing (kg/cm$^2$) |
| 0 | 0.25 | — |
| 1 | 3.7 | 0.7 |
| 2 | 4.0 | 1.5 |
| 3 | 3.8 | 3.0 |
| 4 | 3.9 | 1.5* |

TABLE 2-continued

| Number of Filtration | Differential Pressure | |
|---|---|---|
| | Before Washing (kg/cm$^2$) | After Washing (kg/cm$^2$) |
| 5 | 3.9 | 3.0 |
| 6 | — | — |

Note:
*Alkali-treatment was performed in combination with back washing with water According to the present invention, an aqueous solution having a very small content of a solid matter can be obtained by filtration using a polyethylene-made porous hollow fiber membrane.

High performance filtration as demanded in the present invention generally involves a problem of clogging of a filter medium, but a combination of filtration using a specific filter membrane and washing under specific conditions according to the present invention makes it possible to sufficiently restore filtrability and to thereby achieve stable purification of a reaction solution for a long period of time.

Further, the present invention realizes regeneration of a filter medium by washing, for example, back washing, in combination with regeneration with chemicals, e.g., alkalis, only once per several filtration operations. As a result, amounts of chemicals to be used can be greatly reduced, and at the same time the amounts of waste water required to be handled can also be much reduced.

While the invention has been described in detail and with reference to specific embodiments thereof, it will be apparent to one skilled in the art that various changes and modifications can be made therein without departing from the spirit and scope thereof.

What is claimed is:

1. A method for purifying a reaction solution obtained by using a microbial cell, an immobilized microbial cell, or an immobilized enzyme as a catalyst in a water medium, which comprises repeatedly filtering the reaction solution to remove fine solid matter using a polyethylene porous hollow fiber membrane having a bubble point of from 1 to 20 kg/cm$^2$, and repeatedly washing the hollow fiber membrane before it has been clogged to such an extent that a differential pressure thereof exceeds 3 kg/cm$^2$.

2. A method as in claim 1, wherein said washing is a back washing with water.

3. A method as in claim 1, wherein the method further includes alkali-treatment of the clogged hollow fiber membrane.

4. A method as in claim 1, wherein the reaction solution is an aqueous acrylamide solution.

5. A method as in claim 1, wherein the porous hollow fiber membrane has a diameter of from 0.3 to 1 mm and a length of from 40 to 200 cm.

6. A method as in claim 1, wherein the porous hollow fiber membrane has a bubble point of from 2 to 8 kg/cm$^2$, and the hollow fiber membrane is washed when it has been clogged to such an extent that the differential pressure is from 0.7 to 1.2 kg/cm$^2$.

7. A method as in claim 6, wherein said washing is a back washing with water.

8. A method as in claim 6, wherein the method further includes alkali-treatment of the clogged hollow fiber membrane.

9. A method as in claim 6, wherein the reaction solution is an aqueous acrylamide solution.

10. A method as in claim 6, wherein the porous hollow fiber membrane has a diameter of from 0.3 to 1 mm and a length of from 40 to 200 cm.

11. A method as in claim 1, wherein the back washing is carried out at a differential pressure of from 1 to 10 kg/cm$^2$.

12. A method as in claim 6, wherein the back washing is carried out at a differential pressure of from 1 to 10 kg/cm$^2$.

13. A method as in claim 3, wherein the alkali-treatment is carried out with an aqueous sodium hydroxide solution at a concentration of from 2 to 30% by weight.

14. A method as in claim 8, wherein the alkali-treatment is carried out with an aqueous sodium hydroxide solution at a concentration of from 2 to 30% by weight.

15. A method as in claim 13, wherein the alkali-treatment is carried out for a period of from 0.1 to 100 hours.

16. A method as in claim 14, wherein the alkali-treatment is carried out for a period of from 0.1 to 100 hours.

* * * * *